United States Patent [19]

Small et al.

[11] Patent Number: 5,139,499

[45] Date of Patent: Aug. 18, 1992

[54] SCREW AND DRIVER

[75] Inventors: Alan A. Small, Canton; Bernard J. Bourque, Taunton, both of Mass.

[73] Assignee: American Cyanamid Company, Stamford, Conn.

[21] Appl. No.: 579,188

[22] Filed: Sep. 5, 1990

Related U.S. Application Data

[63] Continuation of Ser. No. 307,343, Feb. 6, 1989, abandoned.

[51] Int. Cl.$^5$ ............................................... A61B 17/58
[52] U.S. Cl. ........................................ 606/73; 606/104
[58] Field of Search ............ 128/92 V, 92 YF, 92 YE, 128/92 R; 81/461, 448, 449, 452; 606/73, 104; 411/394, 395, 407, 408

[56] References Cited

U.S. PATENT DOCUMENTS

| | | | |
|---|---|---|---|
| 1,410,088 | 3/1922 | White | 81/448 |
| 2,593,622 | 4/1952 | Stanelle | 81/448 |
| 2,686,447 | 8/1954 | Vock et al. | 81/461 X |
| 2,775,913 | 1/1957 | Deliso | 81/448 |
| 3,289,290 | 12/1966 | Sandor | 411/407 X |
| 4,171,662 | 10/1979 | Simone et al. | 411/408 |
| 4,325,153 | 4/1982 | Finnegan | 81/461 X |
| 4,950,270 | 8/1990 | Bowman et al. | 606/73 X |

FOREIGN PATENT DOCUMENTS

| | | | |
|---|---|---|---|
| 940375 | 6/1980 | U.S.S.R. | 128/92 V |
| 1097307 | 6/1984 | U.S.S.R. | 128/92 V |
| 940376 | 2/1985 | U.S.S.R. | 128/92 V |

OTHER PUBLICATIONS

Zimmer Advertisement Jul. 1956.
Mueller & Co. Bone Surg. Instr. Nov. 1937.

*Primary Examiner*—Robert A. Hafer
*Assistant Examiner*—Kevin G. Rooney
*Attorney, Agent, or Firm*—Pandiscio & Pandiscio

[57] ABSTRACT

A screw and driver combination designed so that the screw is releasably axially couplable with the driver and so that the screw is positively rotatably engageable with the driver. The screw comprises an axial bore of circular cross section and a counterbore of polygonal cross section. The driver comprises a radially-compressible front portion sized to engage the axial bore of the screw with a minor spring interference fit and an intermediate portion sized to positively rotatably engage the counterbore of the screw. The screw and driver may be adapted for use with a guide wire insertion system by providing axial bores extending through the entire lengths of the screw and driver. The driver may include a mechanical expansion assembly for causing said said front portion to expand radially.

26 Claims, 4 Drawing Sheets

SCREW AND DRIVER

This is a continuation of U.S. Pat. application Ser. No. 07/307,343, filed Feb. 6, 1989, and now abandoned.

FIELD OF THE INVENTION

The present invention relates to screw and driver assemblies, and more particularly to surgical screw and driver assemblies designed so that the driver is releasably couplable to the screw.

BACKGROUND OF THE INVENTION

In certain situations, it is desirable that a screw be both rotationally as well as axially releasably couplable with a driver. For instance, in limited-access work applications, e.g., in arthroscopic or other "closed" surgeries, where a screw is to be inserted into a hole which is not readily accessible, it is advantageous to axially couple the screw with the driver before inserting the screw into the surgical site. Such axial coupling is also beneficial where the screw implantation site is accessible, e.g. where the screw is inserted in a downwardly facing hole.

With such screw and driver combinations, the screw is first attached to the driver and then the driver is manipulated until the screw contacts the implantation site, whereupon the driver is rotated until the screw is fully implanted. Then, the driver is disengaged from the screw by pulling it axially away from the screw.

Such screw and driver combinations are known in the art, as illustrated by U.S. Pat. Nos. 2,329,398, 2,511,051, 2,775,913, 3,463,209, 3,695,321, and 3,888,144. Known screw and driver combinations typically suffer from one or more problems which limit their utility and acceptance in certain situations. For instance, known screw and driver assemblies when designed to provide sufficient axially locking engagement can be difficult to operate, inasmuch as the driver must be inserted with an unacceptably large axial force to overcome the frictional interference between screw and driver. With some screw and driver combinations, the rotational engagement between the screw and driver is not sufficiently positive, i.e., there often is an unacceptably large amount of play between the screw and driver. Other screw and driver combinations (1) tend to be relatively expensive to produce due to the relatively complex shapes of the screw and driver and (2) can permit some axial wobble between screw and driver, i.e., the combination is not designed to ensure the driver is always perfectly co-axially aligned with the screw.

SUMMARY OF THE INVENTION

An object of the present invention is to provide a screw and driver combination designed (a) to provide positive rotational engagement between screw and driver, (b) to permit the driver to be securely attachable to the screw so that the driver is restrained from moving axially relative to the screw while at the same time permitting the driver to be relatively easily attachable to and detachable from the screw, and (c) to ensure the screw and driver when engaged remain co-axially aligned with one another.

Another object of the present invention is to provide a screw and driver combination achieving the foregoing objects which is adapted for use with a "K-wire" or other guide wire insertion system.

These and other objects are achieved by a screw and driver combination comprising a screw and a driver designed to rotatably drive the screw. The latter is preferably, although not necessarily, threaded along its entire length, comprises an axial bore of circular cross section which is open to the top end of the screw and a counterbore of polygonal, preferably hexagonal, cross-section which is also open to the top end of the screw.

The driver comprises an elongate shaft terminating in a radially-compressible cylindrical front portion. The latter is sized and configured so that when the front portion is inserted through the counterbore into the axial bore of the screw, the front portion will compress radially. When the front portion is fully inserted, it snugly engages the wall of the axial bore with a minor spring-biased interference, whereby the driver is releasably coupled in an axial sense, to the screw.

The driver also comprises an elongate intermediate portion having a polygonal, preferably hexagonal, cross-section with the cross-sectional configuration and dimension of the intermediate portion being substantially equal to the cross-sectional configuration and dimension of the counterbore of the screw. The intermediate portion is attached to the rear end of the front portion and the front end of the shaft. Thus, when the front portion is inserted in the axial bore of the screw and the intermediate portion is inserted in the counterbore, by rotating the shaft rotational drive is transmitted, via the engagement of the intermediate portion and the counterbore, to the screw.

BRIEF DESCRIPTION OF THE DRAWINGS

For a fuller understanding of the nature and objects of the present invention, reference should be made to the following detailed description which is to be considered together with the accompanying drawings.

In the drawings, like reference numerals refer to like parts.

DETAILED DESCRIPTION OF THE INVENTION

Figure 1:
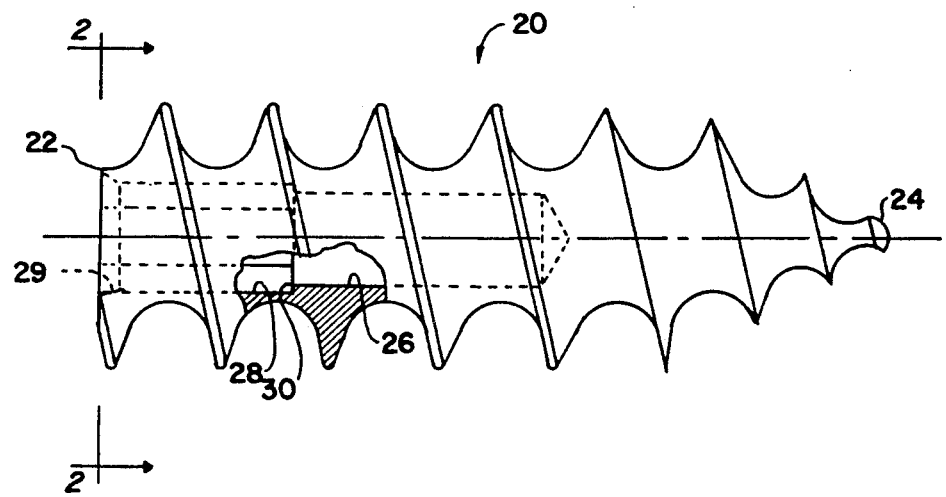
FIG. 1 is a side elevation view, partially broken away, of the screw of the present invention.
Figure 2:
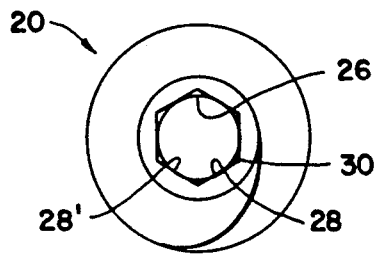
FIG. 2 is an end view of the screw taken along line 2—2 in FIG. 1.
Figure 3:
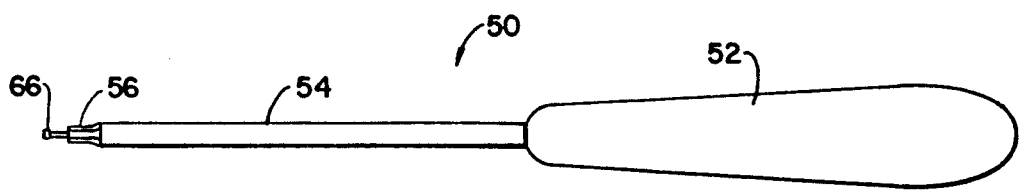
FIG. 3 is a side elevation of the driver of the present invention.

Referring to FIGS. 1-3, the present invention is a screw and driver combination consisting of screw 20 and driver 50.

Screw 20 comprises an elongate shaft having a flat back end 22 and a pointed front end 24. Screw 20 is preferably cylindrical along the majority of its length, with the front portion of the screw tapering down to pointed front end 24. Thus, screw 20 preferably does not comprise a distinct head having a diameter which is greater than the diameter of the shaft of the screw. Alternatively, where the application so requires, a head (not shown) may be attached to back end 22.

Screw 20 is threaded along the entire length of its outside surface. The specific thread pitch will, of course, vary with application and screw size, although for a screw designed for use in arthroscopic or other closed surgeries and having a length of about one inch (1") a thread pitch of about 0.110 inches/thread is satisfactory.

Screw 20 comprises a blind axial bore 26 which is open to back end 22. Axial bore 26 has a circular cross-section, with the diameter of the axial bore preferably being equal to roughly one-third the outside diameter of screw 20. The length of axial bore 26 is preferably equal to about two-thirds the overall length of screw 20.

Screw 20 also comprises a blind counterbore 28 which is co-axial with axial bore 26 and is open to back end 22. Counterbore 28 has a polygonal, preferably hexagonal, cross-section with the result that the counterbore comprises a plurality of flat elongate adjoining faces 28'. Counterbore 28 is dimensioned so that the diameter of a circle contacting simultaneously all of the flat faces 28' of the counterbore is at least as large as the diameter of axial bore 26, and in most cases is larger than the diameter of axial bore 26. As a result of this dimensioning, a seat 30 is formed at the base of counterbore 28. The length of counterbore 28 relative to the portion of axial bore 26 having a circular cross section may vary based on known design parameters, although in an exemplary screw 20 the portion of bore 26 having a circular cross section is approximately one-and-a-half times as long as counterbore 28. A tapered recesses 29 is preferably provided at the mouth of counterbore 28.

As used hereinafter, bore 26 shall refer to the portion of bore 26 having a circular cross section, i.e. the portion of bore 26 between seat 30 and the blind end of the bore, unless specifically mentioned otherwise.

Figure 4:
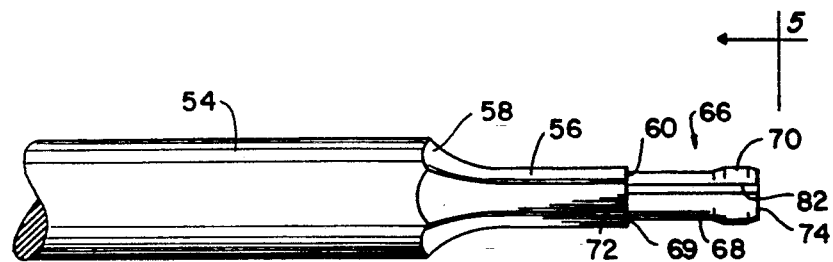
FIG. 4 is an enlarged view of the front portion of the driver illustrated in FIG. 3.
Figure 5:
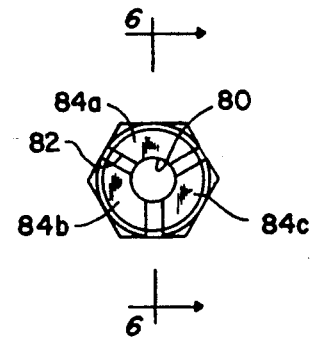
FIG. 5 is an enlarged cross-sectional view taken along line 5—5 in FIG. 4.

Turning now to FIGS. 3-5, driver 50 comprises a handle 52 and an elongate shaft 54 attached to the front end of the handle. Where screw 20 and driver 50 are intended to be used in closed surgeries, the outside diameter of shaft 54 must be selected so that the latter can be freely inserted into and removed from a conventional cannula. The length of shaft 54 will, of course, vary with application.

The front end of shaft 54 tapers to a reduced diameter intermediate portion 56. The latter has a polygonal cross-section, the specific polygonal shape of which corresponds to the polygonal configuration of the cross-section of counterbore 28 in the screw 20 with which the driver 50 is adapted for use. For instance, if counterbore 28 has a hexagonal cross-sectional configuration, then intermediate portion 56 also has a hexagonal cross-section. Furthermore, intermediate portion 56 is dimensioned to be freely slidably insertable into and removable from counterbore 28. At the same time, intermediate portion 56 is dimensioned so that when it is inserted in counterbore 28 it positively engages the sidewall of the counterbore so that rotational drive can be transmitted from intermediate portion 56 to screw 20 with minimal lost motion.

As noted above, intermediate portion 56 has a reduced outside diameter relative to shaft 54. Intermediate portion 56 joins shaft 54 with a smoothly tapering radius portion 58. Preferably, although not necessarily, the polygonal cross-section of intermediate portion 56 is carried through tapering radius portion 58 and terminates at the junction of the radius portion with shaft 54. The length of intermediate portion 56, as measured between the front end 60 of the intermediate portion and front end of radius portion 58, is roughly equal to the length of counterbore 28.

Driver 50 further comprises an elongate, radially-compressible front portion 66 having a central portion 68 and a radially-projecting tip portion 70. Central portion 68 is cylindrical in exterior configuration when not in the compressed state, and is attached at its rear end 72 to front end 60 of intermediate portion 56 so that the axes of elongation of front portion 66 and intermediate portion 56 are co-axial. The diameter of the central portion 68 is less than the diameter of a circle circumscribing intermediate portion 56, with the result that a shoulder 69 (FIG. 4) is formed at the junction of the central portion and the intermediate portion. Preferably, front portion 66 is slightly, e.g. 0.05", shorter than bore 26.

Tip portion 70 is co-axial and integral with central portion 68, and is positioned adjacent front end 74 of front portion 66. Tip portion 70 has a generally cylindrical exterior configuration, with the outside diameter of the tip portion being slightly greater than (i.e. 0.0005–0.0015 inches) the diameter of axial bore 26 in screw 20 when the tip portion is not in the compressed state. Tip portion 70 tapers radially inwardly (a) at its front end to intersect front end 74 and (b) at its rear end to intersect central portion 68.

Front portion 66 further comprises an axial bore 80 which extends along the entire length of the front portion. The inside diameter of axial bore 80 is roughly half the outside diameter of central portion 68.

Front portion 66 also includes three slots 82 extending along the length of the front portion and coupling axial bore 80 with the outside surface of the front portion. Each slot 82 is angularly spaced about the circumference of front end 74 so as to be spaced 120° from the two adjacent slots, whereby front portion 66 is divided into three equally-sized elongate segments 84a, 84b and 84c.

Figure 6:
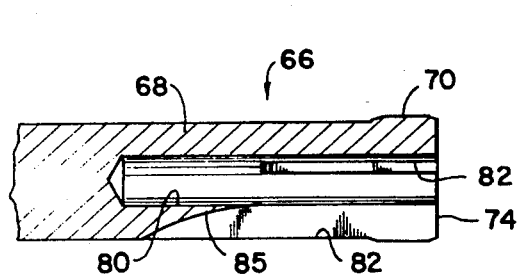
FIG. 6 is a cross-sectional view of the driver taken along line 6—6 in FIG. 5.

Preferably, although not necessarily, as best seen in FIG. 6, the length of the radially-outermost portion of each slot 82 is about equal to the length of axial bore 80, while the length of the radially-innermost portion of each slot 82 is about equal to two-thirds the length of axial bore 80. The wall of front portion 66 in which slots 82 are provided tapers along a gradual radius between the radially-innermost and radially-outermost portions of the slots, as illustrated at 85 in FIG. 6. Alternatively, the radially-innermost and radially-outermost portions of each slot 82 may be the same length or may be related in length by a relationship of other than two-thirds to one. The width of slots 82 is approximately equal to one quarter the diameter of axial bore 80.

As described in greater detail hereinafter, axial bore 80 and slots 82 are provided to allow front portion 66 to be compressed radially inwardly. When a radially compressive force is applied to front portion 66, segments 84a, 84b and 84c will move toward one another. The diameter of axial bore 80, the outside diameter of tip portion 70 when in the uncompressed state, and the width and number of slots 82 are selected so that tip portion 70 will snugly engage the wall of axial bore 26 with a minor spring interference fit when inserted in bore 26. In this compressed state, the front ends of segments 84a, 84b and 84c are driven toward one another so that the width of the front ends of slots 82 is reduced somewhat.

Front portion 66 is made from a material which can readily accommodate, without fatigue or shear, repeated compression and release of segments 84a, 84b and 84c. This material is also sufficiently resilient and has sufficient spring memory so that when segments 84a, 84b and 84c are radially compressed, the segments attain a radially-outwardly acting spring bias. Suitable materials having these properties include stainless steel and titanium.

Figure 7:
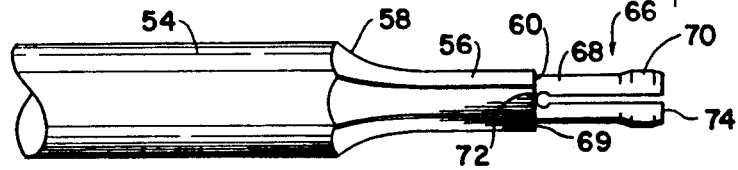
FIG. 7 is an enlarged side elevation view of an alternative version of the front portion of the driver.
Figure 9:
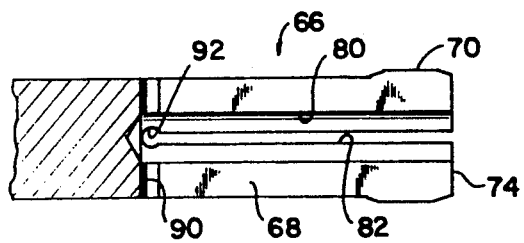
FIG. 9 is a cross-sectional view of the front portion illustrated in FIG. 8 taken along line 9—9 in FIG. 8.
Figure 8:
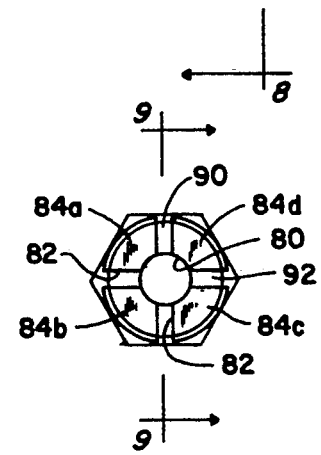
FIG. 8 is an enlarged cross-sectional view of the front portion illustrated in FIG. 7 taken along line 8—8 in FIG. 7.

Referring now to FIGS. 7-9, in an alternative embodiment of front portion 66, four slots 82 are provided in the front portion. Each of the slots 82 is spaced 90° from adjacent slots, as measured around the circumference of front end 74. As such, front portion 66 is divided into four equally-sized, elongate segments 84a, 84b, 84c and 84d, and each slot 82 is diametrically opposite a twin slot 82. The radially innermost as well as the radially outermost portions of slots 82 of the alternative embodiment of front portion 66 extend substantially the entire length of front portion 66, unlike the slots of the embodiment illustrated in FIGS. 4-6 (where the radially-outermost portion of the slot is preferably longer than the radially-innermost portion of the slot, as indicated at 85 in FIG. 6).

Front portion 66 comprises a pair of transverse bores 90 and 92 extending entirely through the thickness of central portion 68. Bore 90 and 92 extend normally to the long axis of front portion 66, intersect the axial bore 80 at the inner end thereof and are perpendicularly aligned with respect to one another. Bore 90 is positioned so that its long axis extends through one of the pairs of diametrically opposed slots 82, and bore 92 is positioned so that its long axis extends through the other of the pairs of diametrically opposed slots 82. The diameters of bore 90 and 92 are identical and are somewhat greater than the width of slots 82. Bores 90 and 92 are provided to prevent the formation of stress fractures at the base of slots 82 which might reduce the resiliency and spring memory of elongate portions 84a, 84b, 84c, and 84d.

The outside diameter of tip portion 70 of the four-slot version of front portion 66 is about 0.0020–0.004 inches, preferably 0.003 inches, greater than the inside diameter of bore 26 of screw 20. Thus, the outside diameter of tip portion 70 of the four-slot version of front portion 66 is slightly greater than the outside diameter of the tip portion 70 of the three-slot version of front portion 66. Tip portion 70 of the four-slot version of front portion 66 has this slightly larger diameter because the provision of four slots 82, as opposed to three slots 82, permits the four slot version of front portion 66 to be more easily radially compressed. As such, to achieve the desired minor spring interference fit between front portion 66 and counterbore 26, the outside diameter of tip portion 70 of the four slot version of front portion 66 is slightly enlarged.

EXAMPLE

An exemplary screw and driver combination of the present invention, designed for use in arthroscopic or other closed surgeries, possesses the following specific dimensions:

Screw 20 overall length: 1.18", outside diameter (measured at radially outermost portion of threads): 0.276", angle of pointed front portion: 30° with respect to longitudinal axis (included angle of 60°) diameter of axial bore 26: "0.0945", polygonal configuration of counterbore: hexagonal, with diametric distance between parallel opposing faces equal to "0.0945", thread pitch: 0.110 inches/thread length of counterbore 28: 0.20" length of axial bore 26: 0.45"

Driver 50 overall length: 9.25", length of shaft 54: 4.00", diameter of shaft 54: 0.187", length of intermediate portion 56 (excluding radius portion 58): 0.20", polygonal configuration of intermediate portion 56: hexagonal, with diametric distance between any two parallel opposing faces equal to: 0.0928, length of front portion 66: 0.20", length of central portion 68: 0.140", diameter of central portion 68 (in uncompressed state): 0.088", diameter of tip portion (in uncompressed state): 0.0955"

length of slots 82 radially innermost edge: 0.120"

radially outermost edge: 0.200"

width of slots 82: 0.010"

number of slots 82: 3

The above-listed dimensions are only exemplary, and may, of course, be varied depending upon the desired application of the present screw and driver combination.

OPERATION

Referring to FIGS. 1–10, the screw and driver combination of the present invention may be satisfactorily used, for example, in a surgical context to secure a bone plug 100 (FIG. 10) in a hole 102 drilled in a bone 104. As is well known, the diameter of hole 102 is selected so that the corners of bone plug 100 will contact the wall of hole 102. Typically, a tendon (not shown) or other tissue is attached to bone plug 100 before it is inserted in hole 102.

After the bone plug 100 has been inserted into hole 102, driver 50 is manipulated relative to screw 20 so that front portion 66 passes through counterbore 28 into axial bore 26 of screw 20. Because the diameter of tip portion 70 in the uncompressed state is slightly greater than the diameter of axial bore 26 of screw 20, front portion 66 must be radially compressed somewhat so that the tip portion can be slidingly inserted into bore 26. To this end, tip portion 70 is provided with an inwardly tapering front end which coacts in cam-like fashion with either (a) tapering recess 29 at the mouth of counterbore 28 when bore 26 and counterbore 28 have similar inside diameters of (b) the mouth of bore 26 (adjacent seat 30) when the inside diameter of bore 26 is greater than the inside diameter of bore 26. Thus, when front portion 66 is urged into bore 26 this cam-like coaction forces segments 84a, 84b and 84c or, 84a-84d in the case of the alternative embodiment illustrated in FIGS. 7-9, radially inwardly. This radially inward compression of front portion 66 permits the latter to be inserted through counterbore 28 and into axial bore 26 with a sliding fit. Because front portion 66 is compressed slightly when received in axial bore 26, tip portion 70 engages the axial bore with a minor spring interference fit.

When front portion 66 is fully inserted in axial bore 26 in screw 20, and the length of the straight, non-tapering section of intermediate portion 56 is greater than or equal to the length of counterbore 28 in screw 20, driver shoulder 69 will engage screw seat 30. When the length of the straight, non-tapering section of intermediate portion 56 is less than the length of counterbore 28, back end 22 of screw 20 adjacent recess 29 will engage radially tapering portion 58 of intermediate portion 56 when front portion 66 is fully inserted in axial bore 26. In either case, this engagement provides feedback to the user as to when the front portion is fully inserted. During the insertion of front portion 66, shaft 54 must be rotated so that the flat faces of intermediate portion 56 are parallel to respective flat faces of counterbore 28 in screw 20. The cross-sectional dimensions of intermediate portion 56 are slightly less than the cross-sectional dimensions of screw counterbore 28 so the intermediate portion can be inserted into the counterbore with an easy sliding fit. The dimensions of intermediate portion 56 relative to the dimensions of counterbore 28 are also selected so that rotational drive can be transmitted from driver 50 to screw 20 with minimal loss of energy.

The pointed front end of screw 20 is then inserted into one of the gaps 106 (FIG. 10) between bone plug 100 and the wall of hole 102. Because screw 20 is coupled with driver 50 as a result of the minor spring interference fit between tip 70 and axial bore 26, the screw may be directed to the opening of the gap 106 solely by appropriate manipulation of driver 50. Where screw 20 is being used in a closed surgery, the screw and driver shaft 54 may be inserted as a unit into an appropriately-positioned cannula, with the driver being manipulated based on information provided by the fiber optic or other viewing system used in conjunction with the closed surgery until the pointed front end of the screw is received in the opening of the gap 106.

Next, driver handle 52 is rotated, causing shaft 54 and intermediate portion 56 to rotate. The latter has the same polygonal configuration as and is approximately the same size as counterbore 28 so that when intermediate portion 56 is rotated it transmits rotational drive to the wall of the counterbore and hence to screw 20. As screw 20 is rotated, its outer threaded surface engages bone plug 100 and the adjacent portion of bone 104 and thereby pulls the screw into the bone and bone plug. When screw 20 is fully implanted it acts as a wedge forcing bone plug 100 into tight frictional engagement with the wall of hole 102.

After screw 20 has been fully inserted, driver 50 is separated from the screw by pulling the driver axially away from the screw. Tip portion 70 resists this axial pulling to some extend so as to ensure the screw and driver do not inadvertently become separated prior to completion of the implantation of the screw. However, when a moderately forceful axial pull is applied, the minor spring interference between tip portion 70 and axial bore 26 is overcome and the driver can be detached from the screw.

FIRST ALTERNATIVE EMBODIMENT

In arthroscopic and other closed surgeries, so called "K" wire or other guide wire systems are used to deliver a surgical fastener to an implantation site. As is known, these systems comprise a long wire, typically having a pointed end, which is inserted into selected tissue in the surgical site. Surgical tools, fasteners and other devices adapted for use with guide wire systems (and hence comprising an axial bore extending entirely through the device) are delivered to the site in the tissue where the wire has been inserted by placing the device on the wire so the latter extends through the axial bore of the device. The device is then moved down the wire until it reaches the tissue.

Figure 11:
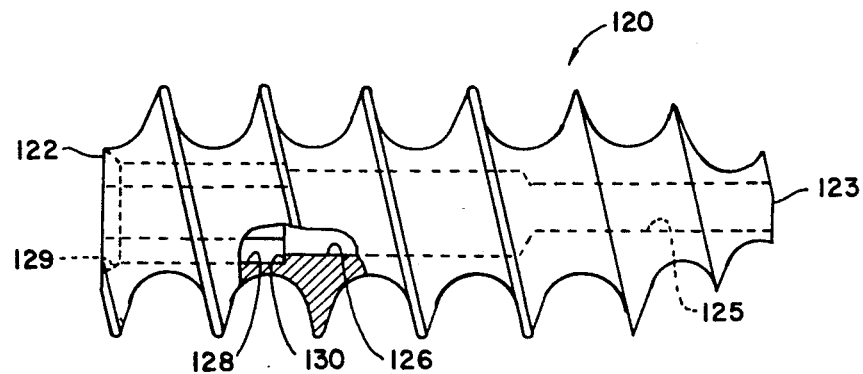
FIG. 11 is a side elevation, partially broken away, of the screw of the first alternative embodiment of the present invention.
Figure 12:
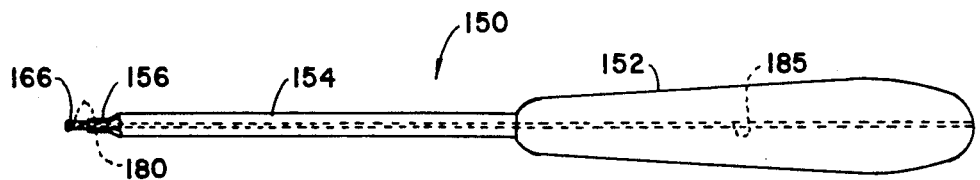
FIG. 12 is a side elevation of the driver of the first alternative embodiment of the present invention.
Figure 13:
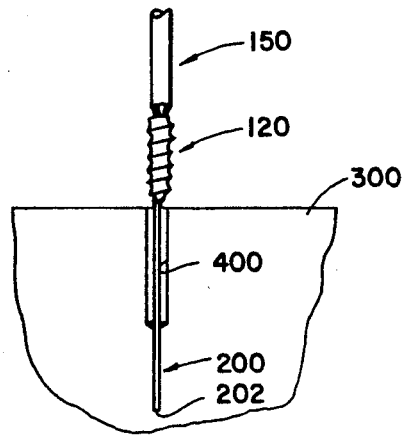
FIG. 13 is a schematic side elevation view showing the screw and driver of the first alternative embodiment, the material in which the screw of the first alternative embodiment is to be implanted, and the guide wire used with the screw and driver of the first alternative embodiment.

Referring not to FIGS. 11-13, screw 120 and driver 150 of the alternative embodiment of the present invention are virtually identical to screw 20 and driver 50 of the first embodiment of the present invention, except that axial bores are provided extending through the entire length of both the screw 120 and driver 150. By providing these axial bores, screw 120 and driver 150 are adapted for use with a guide wire system of the type described above.

Describing screw 120 in greater detail, the latter has a cylindrical configuration, with the pointed front end of the screw terminating in a blunt tip 123. The exterior surface is threaded, as described above with reference to screw 20. Screw 120 comprises an axial bore 125 which extends through the entire length of the screw. The pointed front end of screw 120 is blunted as a result of the passage of bore 125 therethrough, with the area of blunt tip 123 being equal to the area of the cross-section of bore 125.

Screw 120 includes a counterbore 126 which is co-axial with axial bore 125 and is open to rear end 122 of the screw. Screw 120 further includes a counterbore 128 which is also co-axial with axial bore 125 and is open to rear end 122 of the screw. A tapered recess 129 is provided in rear end 122 at the mouth of counterbore 128.

The length, diameter and cross-sectional configuration of counterbores 126 and 128 are equal to the length and diameter of bore 26 and counterbore 28, respectively, of screw 20. The diameter of axial bore 125 is somewhat greater than the diameter of the guide wire with which screw 120 and driver 150 are to be used, so that the screw can slide freely along the wire. Thus, for example, for a guide wire having a diameter of 0.035", axial bore 125 should have a diameter of about 0.045". In any event, the diameter of axial bore 125 is always less than or equal to the diameter of counterbore 126.

Thus, in every detail, except for the provision of axial bore 125 and the resultant blunt tip 123, screw 120 is identical to screw 20.

Referring to FIG. 12, driver 150 comprises a handle 152, an elongate shaft 154 attached to the handle, an intermediate portion 156 attached to the front end of the elongate shaft, and a front portion 166 attached to the front end of the intermediate portion. An axial bore 180 extends through the entire length of front portion 166. Elements 152–156, 166 and 180 are identical in length, diameter and cross-sectional configuration to corresponding elements 52–56, 66 and 80 of driver 50.

Driver 150 differs from driver 50 only in that the former comprises a central axial bore 185 extending through the entire length of driver 150. Thus, central bore 185 extends through handle 152, shaft 154, intermediate portion 156 and front portion 166. Although axial bore 180 can be regarded as a counterbore with respect to axial bore 185, in most cases central bore 185 and axial bore 180 will be coextensive inasmuch as the diameter of central bore 185 is preferably identical to the diameter of axial bore 180. The diameters of axial bore 180 and central bore 185 are, of course, somewhat greater than the diameter of the guide wire with which screw 120 and driver 150 are to be used.

Thus, in every detail, except for the provision of central bore 185, driver 150 is identical to driver 180.

Referring now to FIGS. 10–13, screw 120 and driver 150 are used in substantially the same manner as screw 20 and driver 50 of the first embodiment, the only difference being screw 120 and driver 150 are delivered to the implantation site using a guide wire system. Thus, prior to inserting screw 120 using driver 150, a long thin guide wire 200 is inserted into the material 300, e.g., tissue such as bone, ligament, or tendon, into which screw 120 is to be implanted. Thus, referring to FIG. 10, if screw 120 is to be implanted in gap 106 between bone plug 100 and the wall of hole 102, then guide wire 200 is inserted into the bone at the bottom of gap 106. If screw 120 is to be inserted into the material 300 surrounding a pilot hole 400 formed in material 300, as illustrated in FIG. 13, then guide wire 200 is inserted into pilot hole 400 so that it penetrates into the material at the base of the pilot hole and is substantially coaxial with respect to the pilot hole.

Guide wire 200 has a diameter of approximately 0.035 inches and its leading tip 202 preferably penetrates tissue 300 to a depth of at least 0.75 inches. It is to be appreciated that the guide wire's leading tip 202 is substantially pointed so that it can more easily penetrate through into material 300. Guide wire 200 may be implanted simply by pushing it into the tissue, or it may be mounted in a drilling device (not shown) to facilitate entry.

In the event the guide wire 200 is intended to be simply pushed into material 300, a supporting cannula of the sort well known in the art (not shown) may be concentrically mounted around at least a portion of the guide wire during insertion so as to help maintain the linear shape of the guide wire during penetration. If such a supporting cannula is used, it is removed from around the guide wire as soon as the guide wire has been properly positioned as shown in FIG. 13. Alternatively, in the event guide wire 200 is intended to be drilled into material 300, the guide wire's leading tip 202 may also include a helical drilling thread (not shown) to facilitate penetration. If a drilling device is used to deploy guide wire 200, the drilling device is detached from the guide wire as soon as the guide wire has been properly positioned in the manner shown in FIG. 13.

Reference should be made to FIGS. 11–13 in connection with the following description of the manner in which screw 120 and driver 150 are used with guide wire 200. First, driver 150 is urged toward screw 120 so that driver front portion 166 enters counterbore 128 of screw 120. Driver 150 is urged toward screw 120 until the driver's intermediate portion 156 reaches the mouth of counterbore 128. At this juncture, driver 150 is rotated so that the flat faces of intermediate portion 156 line up with the corresponding respective flat faces of counterbore 128 of screw 120. Thereafter, driver 150 is urged toward screw 120 causing intermediate portion 156 of driver 150 to enter screw counterbore 128 and driver front portion 166 to enter screw counterbore 126. As discussed above with respect to driver 50, when front portion 166 is inserted into counterbore 126, front portion 166 is radially compressed slightly so that the front portion 166 engages the wall of the counterbore 126 with a minor spring interference fit.

When front portion 166 of driver 150 is inserted in screw 120 in this manner, by rotating driver 150, typically via handle 152, rotational drive is transmitted from driver 150 to the screw as a result of the positive rotational engagement between intermediate portion 156 of driver 150 and the wall of counterbore 128 of screw 120. Additionally, screw 120 and driver 150 are releasably coupled in an axial sense as a result of the minor spring interference between driver front portion 166 and the wall of counterbore 126 of screw 120.

Next, screw 120 and driver 150 are loaded concentrically onto guide wire 200, with the screw's front tip 123 leading, so that the guide wire passes through the screw's axial bore 125 and the driver's central bore 185. Screw 120 is then delivered to pilot hole 400 by moving the coupled screw and driver combination down guide wire 200 until tip 123 of screw 120 contacts the portions of material 300 surrounding the opening of the pilot hole, as illustrated in FIG. 13. Driver 150 is then rotated, which in turn causes screw 120 to rotate, whereby the screw thread on the exterior of screw 120 engages material 300 and pulls the screw into the material. Driver 150 is rotated until the screw is either partially or fully implanted in material 300, as desired. Driver 150 is then separated from screw 120 by pulling the driver away from the screw with a force sufficient to overcome the minor spring interference between driver front portion 166 and screw counterbore 126. After removing driver 150 from guide wire 200, the latter is withdrawn from pilot hole 400 leaving screw 120 firmly implanted in material 300. This completes the screw implantation procedure using the screw and driver combination of the alternative embodiment.

Figure 10:
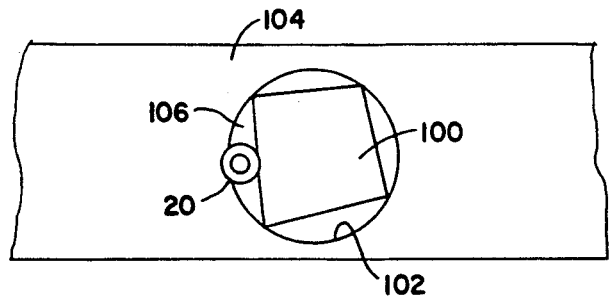
FIG. 10 is a plan view showing the screw of the present invention inserted into a gap between a bone plug and the wall of the hole in the bone in which the bone plug is inserted.

Referring to FIG. 10, a similar implantation procedure is followed when screw 120 is to be implanted into gap 106 between bone plug 100 and the wall of hole 102 in bone 104, the only difference being guide wire 200 is positioned in gap 106 instead of in pilot hole 400.

SECOND ALTERNATIVE EMBODIMENT

Figure 16:
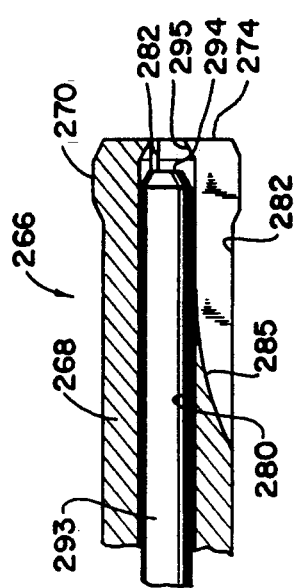
FIG. 16 is a side elevation, taken in cross section, of the front portion of another version of the driver of the second alternative embodiment.
Figure 14:
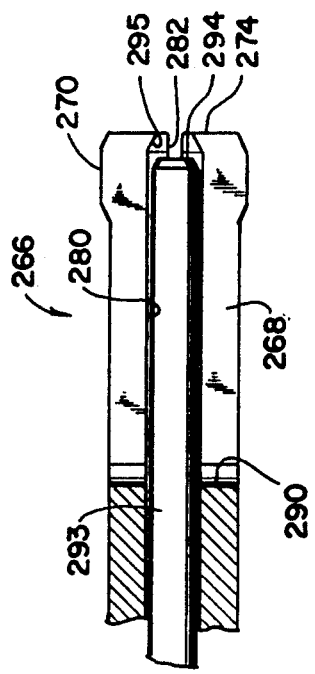
FIG. 14 is a side elevation, taken in cross section, of the front portion of one version of the driver of the second alternative embodiment.

Under certain circumstances it may be desirable to force elongate sections 84a–84c or 84a–84d, as the case may be, of front portion 66 radially outwardly. To achieve this function, a second alternative embodiment of the present invention is provided consisting of driver 250 illustrated in FIGS. 14–16. Driver 250 comprises a handle 252, an elongate shaft 254, an intermediate portion 256, and a front portion 266. The latter comprises a central portion 268, a tip portion 270, and terminates at front end 274. Three or four slots 282 are provided extending along the length of front portion 266 and coupling the exterior surface of front portion 266 with axial bore 280 which runs the entire length of front portion 266. Elements 252, 254, 256, 266, 268, 270, 274, 280, and 282 are identical in size, configuration and number, as the case may be, respectively, to elements 52, 54, 56, 66, 68, 70, 74, 80, and 82 of driver 50 illustrated in FIGS. 3-9 and described above.

Driver 250 differs from driver 50 in several respects. First, axial bore 280 is extended rearwardly through intermediate portion 266, shaft 254 and into at least the front portion of handle 252.

Second, an elongate shaft 293 is disposed in axial bore 280. The outside diameter of shaft 293 is selected so that the latter slides freely inside axial bore 280. Shaft 293 terminates in a blunt end 294.

Third, the front end of axial bore 280 tapers radially inwardly adjacent front end 274 as indicated at 295.

Fourth, a transverse slot 296 is provided in handle 252 coupling axial bore 280 with the outside surface of the handle.

Figure 15:
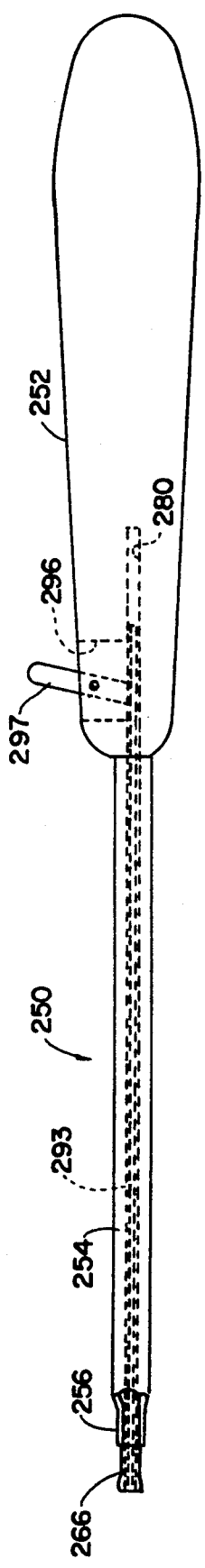
FIG. 15 is a side elevation of the driver of the second alternative embodiment.

Fifth, a lever 297 is pivotally mounted in slot 296 so as be to rotatable about an axis extending perpendicular to the long axis of shaft 254. One end of lever 297 is flexibly attached to the rear end of shaft 293 and the other end of the lever projects out of slot 296 away from the exterior surface of handle 252. Lever 297 is mounted and attached in this fashion so that by moving the protruding portion of lever 297 toward front portion 266, shaft 293 is caused to move rearwardly in axial bore 280 away from front end 274 of front portion 266. Similarly, by moving the protruding portion of lever 297 away from front portion 266, shaft 293 is caused to move forwardly in axial bore 280 toward front end 274. Shaft 293 is sized so that when the protruding portion of lever 297 is moved rearward of the vertical position, as seen in FIG. 15, blunt end 294 of shaft 293 will contact the radially-inwardly tapering portion 295 of axial bore 280. Further rearward movement of lever 297 causes blunt end 294 to move forward relative to tapering portion 295, whereby the blunt end coacts with the tapering portion in cam-like fashion causing front portion 266 to expand radially. Shaft 293 is also sized so that when lever 297 is moved forward of the vertical position, as seen in FIG. 15, blunt end 294 of shaft 293 will not contact tapering portion 295.

These differences between driver 250 and driver 50 exist for both the four slot version (FIG. 14) and the three slot version (FIG. 16) of front portion 266.

Optionally, axial bore 280 may be extended to the rear end of handle 252 and a bore may be provided in shaft 293 so that driver 250 can be used with a guide wire 200 of the type described above and illustrated in FIG. 13.

Driver 250 is adapted for use with screw 20 described above, and functions in a similar manner to driver 50. The only difference in operation between driver 250 and driver 50 is that the former, after being rotationally and axially coupled to screw 20, is actuated to cause front portion 266 to expand radially and thereby securely axially couple the front portion with the wall of bore 26 of screw 20. This actuation is effected by moving the protruding portion of lever 297 rearwardly so as to cause blunt end 294 of shaft 293 to move forwardly and coact in cam-like fashion with tapering portion 295. This coaction causes front portion 266 to expand radially.

An important advantage of the screw and driver combination of the present invention is that front portion 66(166, 266) is designed to engage bore 26(126) of screw 20(120) with both an interference as well as a spring fit. This mode of engagement is advantageous in that it provides a secure axial coupling between screw and driver and yet permits the driver to be withdrawn from the screw without the need to apply an unacceptably large axial force to the driver. Additionally, by sizing the front portion 66(166, 266) and bore 26(126) so that they engage one another with an interference fit, the limitations associated with a solely spring-biased engagement, e.g., loss of resiliency with use, are avoided.

The first alternative embodiment of the present invention which is designed for use with a guide wire system is advantageous in that it facilitates quick and easy axial alignment of the screw with the pilot hole. This ease of alignment is especially important where the screw is to be inserted in a pilot hole which is relatively inaccessible, e.g. a pilot hole located deep in a arthroscopy site.

The second alternative embodiment of the present invention is advantageous in that axially coupling between screw and driver is achieved by interference fit, spring bias and positive mechanical locking. By designing the driver 250 to include these three means for axially coupling the screw thereto, the material characteristics for driver 250 become less critical inasmuch as the spring memory characteristics of the material are less important.

Since certain changes may be made in the above-described screw and driver without departing from the scope of the invention herein involved, it is intended that all matter contained in the above description or shown in the accompanying drawings shall be interpreted in an illustrative and not in a limiting sense.

What is claimed is:

1. A screw an driver combination comprising:
   an elongate screw including
   (a) first and second ends,
   (b) an axial bore coupled with said first end, said axial bore having a circular cross section of selected diameter, and
   (c) a counterbore coupled with said first end and coaxial with said axial bore, said counterbore having a selected length and a polygonal cross section of selected configuration and dimension; and
   a driver including
   (a) an elongate shaft having a front end,
   (b) an elongate intermediate portion having first and second ends, said second end of said intermediate portion being fixedly attached to said front end of said shaft, said intermediate portion having a polygonal cross section configured and dimensioned (i) so that said intermediate portion can be inserted into said counterbore of said screw with a sliding fit and (ii) so that when said intermediate portion is inserted in said counterbore said intermediate portion drivingly engages said counterbore so that rotational drive can be transmitted from said driver to said screw, and
   (c) a cylindrical front portion having a back end and a front end, said back end of said front portion being fixedly attached to said first end of said intermediate portion, said front portion comprising compression means for permitting said front portion to be compressed radially into a compressed state, the design and diameter of said cylindrical front portion being chosen (i) so that insertion of said front portion into said bore of said screw causes said front portion to be compressed into said compressed state, and (ii) so that when said front portion is inserted in said bore said front portion engages said bore with a spring interference fit, whereby said front portion cannot be removed from said bore except when a selected axial force is applied to said front portion.

2. A combination according to claim 1 wherein said compression means comprises:
an axial bore in said front portion coupled with said front end of said front portion and extending substantially the entire length of said front portion; and
a plurality of axially-extending slots in said front portion coupling said axial bore of said front portion with the exterior surface of said front portion.

3. A combination according to claim 2 wherein said plurality of slots comprises three slots.

4. A combination according to claim 2 wherein said plurality of slots comprises four slots.

5. A combination according to claim 1 wherein the length of said intermediate portion is greater than the length of said counterbore and the length of said front portion is less than the length of said axial bore minus the length of said counterbore.

6. A combination according to claim 1 wherein said intermediate portion is attached to said shaft and said front portion is attached to said intermediate portion so that the axes of elongation of said shaft, said intermediate portion and said front portion are coaxial.

7. A combination according to claim 1 wherein said second end of said screw is pointed.

8. A combination according to claim 1 wherein said cylindrical front portion comprises a central portion and a tip portion, the outside diameter of said tip portion being slightly greater than the inside diameter of the portion of said axial bore of said screw having a circular cross section when said front portion is not in said compressed state, and the outside diameter of said central portion being less than the outside diameter of said tip portion regardless of whether or not said front portion is in said compressed state.

9. A combination according to claim 1 wherein the outside diameter of said front portion is slightly greater than the inside diameter of the portion of said axial bore of said screw having a circular cross section when said front portion is not in said compressed state.

10. A combination according to claim 1 wherein a screw thread is disposed on the exterior surface of said screw extending along the entire length of said screw.

11. A combination according to claim 1 wherein the configuration of the cross section of said intermediate portion of said drive and said counterbore of said screw is hexagonal.

12. A combination according to claim 1 wherein said screw comprises a central bore extending through the entire length of said screw, and said driver comprises a central bore extending through the entire length of said driver.

13. A screw and driver combination designed for use with an elongate guide wire, the combination comprising:

an elongate screw including
(a) first and second ends,
(b) an axial bore extending through the entire length of said screw, with the diameter of said axial bore being greater than the diameter of a guide wire adapted for insertion into the material into which the screw is to be implanted,
(c) a counterbore coupled with said first end and coaxial with said axial bore, said counterbore having an inner axial portion with a circular cross section of selected diameter, and an outer axial portion coupled with said first end and having a polygonal cross section of selected configuration and dimension; and a driver including
(a) an elongate shaft having a front end,
(b) an elongate intermediate portion having first and second ends, said second end of said intermediate portion being fixedly attached to said front end of said shaft, said intermediate portion having a polygonal cross section configured and dimensioned (i) so that said intermediate portion can be inserted into said outer axial portion of said counterbore of said screw with a sliding fit and (ii) so that when said intermediate portion is inserted in said outer axial portion of said counterbore said intermediate portion drivingly engages said outer axial portion of said counterbore so that rotational drive can be transmitted from said driver to said screw,
(c) a cylindrical front portion having a back end and a front end, said back end of said front portion being fixedly attached to said first end of said intermediate portion, said front portion comprising compression means for permitting said front portion to be compressed radially into a compressed state, the design and diameter of said cylindrical front portion being chosen (i) so that insertion of said front portion into said inner axial portion of said counterbore of said screw causes said front portion to be compressed into said compressed state, and (ii) so that when said front portion is inserted in said inner axial portion of said counterbore said front portion engages said inner axial portion of said counterbore with a spring interference fit, whereby said front portion cannot be removed from said inner axial portion of said counterbore except when a selected axial force is applied to said front portion, and
(d) an axial bore extending through the entire length of said driver, said axial bore having a diameter greater than the diameter of said guide wire.

14. A system for use in implanting a screw into selected material, the system comprising:
an elongate guide wire adapted to be inserted into selected material in which said screw is to be implanted;
an elongate screw including
(a) first and second ends,
(b) an axial bore extending through the entire length of said screw, with the diameter of said axial bore being greater than the diameter of said guide wire,
(c) a counterbore coupled with said first end and coaxial with said axial bore, said counterbore having an inner axial portion with a circular cross section of selected diameter, and an outer axial portion coupled with said first end and having a polygonal cross section of selected configuration and dimension; and a driver including
  (a) an elongated shaft having a front end,
  (b) an elongate intermediate portion having first and second ends, said second end of said intermediate portion being fixedly attached to said front end of said shaft, said intermediate portion having a polygonal cross section configured and dimensioned (i) so that said intermediate portion can be inserted into said outer axial portion of said counterbore of said screw with a sliding fit and (ii) so that when said intermediate portion is inserted in said outer axial portion of said counterbore said intermediate portion drivingly engages said outer axial portion of said counterbore so that rotational drive can be transmitted from said driver to said screw,
  (c) a cylindrical front portion having a back end and a front end, said back end of said front portion being fixedly attached to said first end of said intermediate portion, said front portion comprising compression means for permitting said front portion to be compressed radially into a compressed state, the design and diameter of said cylindrical front portion being chosen (i) so that insertion of said front portion into said inner axial portion of said counterbore of said screw causes said front portion to be compressed into said compressed state, and (ii) so that when said front portion is inserted in said inner axial portion of said counterbore said front portion engages said inner axial portion of said counterbore with a spring interference fit, whereby said front portion cannot be removed from said inner axial portion of said counterbore except when a selected axial force is applied to said front portion, and
  (d) an axial bore extending through the entire length of said driver, said axial bore having a diameter greater than the diameter of said guide wire.

15. A screw and driver combination comprising:
an elongate screw including
  (a) a first end and a pointed second end,
  (b) an axial bore coupled with said first end, said axial bore having a circular cross section of selected diameter, and
  (c) a counterbore coupled with said first end and coaxial with said axial bore, said counterbore having a selected length and a hexagonal cross section of selected dimension, wherein a screw thread is disposed on the exterior surface of said screw extending along the entire length of said screw; and
a driver including
  (a) an elongate shaft having a front end,
  (b) an elongate intermediate portion having first and second ends, said second end of said intermediate portion being fixedly attached to said front end of said shaft so that said shaft and said intermediate portion are coaxially aligned, said intermediate portion having a hexagonal cross section configured and dimensioned (i) so that said intermediate portion can be inserted into said counterbore of said screw with a sliding fit and (ii) so that when said intermediate portion is inserted in said counterbore said intermediate portion drivingly engages said counterbore so that rotational drive can be transmitted from said driver to said screw, and
  (c) a cylindrical front portion having a back end and a front end, said back end of said front portion being fixedly attached to said first end of said intermediate portion so that said intermediate portion and said front portion are coaxially aligned, said front portion comprising compression means for permitting said front portion to be compressed radially into a compressed state, the design and diameter of said cylindrical front portion being chosen (i) so that insertion of said front portion into the section of said bore of said screw having a circular cross section causes said front portion to be compressed into said compressed state, and (ii) so that when said front portion is inserted in said section of said bore having a circular cross section said front portion engages said section with a spring interference fit, whereby said front portion cannot be removed from said section except when a selected axial force is applied to said front portion,
said compression means comprising
  (a) an axial bore in said front portion coupled with said front end of said front portion and extending substantially the entire length of said front portion and
  (b) a plurality of axially-extending slots in said front portion coupling said axial bore of said front portion with the exterior surface of said front portion, and further wherein said front portion comprises a central portion and a tip portion, the outside diameter of said tip portion being slightly greater than the inside diameter of said section of said axial bore of said screw having a circular cross section when said front portion is not in said compressed state, and the outside diameter of said central portion being somewhat less than the outside diameter of said tip portion regardless of whether or not said front portion is in said compressed state.

16. A combination according to claim 1 wherein said driver further comprises:
expansion means movable between a first position and a second position for coacting with said front portion of said driver so as to cause said front portion to expand radially when said expansion means is moved toward said second position; and
actuation means coupled to said expansion means for causing said expansion means to move between said first position and said second position.

17. A combination according to claim 16 wherein said actuation means comprises:
an axial bore in said driver extending through said front portion, said intermediate portion, and at least a front section of said handle, said bore being open to said front end of said front portion, said bore comprising a radially-inwardly tapering section adjacent said front end of said front portion;
a shaft disposed in said axial bore and sized to be freely slidable along the entire length of said axial bore except for within said radially-inwardly tapering section of said axial bore, said shaft having a front end, said shaft being additionally sized so that when said front end of said shaft is urged into said radially-inwardly tapering section of said axial bore said shaft coacts with said radially-inwardly tapering section in cam-like fashion so as to cause said front portion to expand radially.

18. A combination according to claim 17 wherein said actuation means comprises lever means mounted adjacent said front section of said handle and coupled to said shaft for causing said shaft to move axially between a first position wherein said front end of said shaft is not disposed within said radially-inwardly tapering section of said axial bore and a second position wherein said front end of said shaft is disposed within the portion of said radially-inwardly tapering portion having the smallest inside diameter.

19. A combination according to claim 17 wherein said axial bore extends through the entire length of said handle and is open to a rear end of said handle, and said shaft comprises a central axial bore extending through the entire length of said shaft.

20. A screw and driver combination comprising:
an elongate screw including
  (a) first and second ends,
  (b) an axial bore coupled with said first end, said axial bore having a circular cross section of selected diameter, and
  (c) a counterbore coupled with said first end and coaxial with said axial bore, said counterbore having a selected length and a polygonal cross section of selected configuration and dimension; and
a driver including
  (a) an elongate shaft having a front end,
  (b) an elongate intermediate portion having first and second ends, said second end of said intermediate portion being attached to said front end of said shaft, said intermediate portion having a polygonal cross section configured and dimensioned (i) so that said intermediate portion can be inserted into said counterbore of said screw with a sliding fit and (ii) so that when said intermediate portion is inserted in said counterbore said intermediate portion drivingly engages said counterbore so that rotational drive can be transmitted from said driver to said screw, and
  (c) a cylindrical front portion having a back end and a front end, said back end of said front portion being attached to said first end of said intermediate portion, said front portion comprising compression means for permitting said front portion to be compressed radially into a compressed state, the design and diameter of said cylindrical front portion being chosen (i) so that insertion of said front portion into said bore of said screw causes said front portion to be compressed into said compressed state, and (ii) so that when said front portion is inserted in said bore said front portion engages said bore with a spring interference fit, whereby said front portion cannot be removed from said bore except when a selected axial force is applied to said front portion,
wherein said driver further comprises:
  expansion means movable between a first position and a second position for coating with said front portion of said driver so as to cause said front portion to expand radially when said expansion means is moved toward said second position; and
  actuation means coupled to said expansion means for causing said expansion means to move between said first position and said second position,
wherein said actuation means comprises:
  an axial bore in said driver extending through said front portion, said intermediate portion, and at least a front section of said handle, said bore being open to said front end of said front portion, said bore comprising a radially-inwardly tapering section adjacent said front end of said front portion; and
  a shaft disposed in said axial bore and sized to be freely slidable along the entire length of said axial bore except for within said radially-inwardly tapering section of said axial bore, said shaft having a front end, said shaft being additionally sized so that when said front end of said shaft is urged into said radially-inwardly tapering section of said axial bore said shaft coacts with said radially-inwardly tapering section in cam-like fashion so as to cause said front portion to expand radially.

21. A combination according to claim 10 wherein said actuation means comprises lever means mounted adjacent said front section of said handle and coupled to said shaft for causing said shaft to move axially between a first position wherein said front end of said shaft is not disposed within said radially-inwardly tapering section of said axial bore and a second position wherein said front end of said shaft is disposed within the portion of said radially-inwardly tapering portion having the smallest inside diameter.

22. A screw and driver combination comprising:
an elongate screw including
  (a) first and second ends,
  (b) an axial bore coupled with said first end, said axial bore having a circular cross section of selected diameter, and
  (c) a counterbore coupled with said first end and coaxial with said axial bore, said counterbore having a selected length and a non-circular cross section of selected configuration and dimension; and
a driver including
  (a) an elongate shaft having a front end,
  (b) an elongate intermediate portion having first and second ends, said second end of said intermediate portion being fixedly attached to said front end of said shaft, said intermediate portion having a non-circular cross section configured and dimensioned (i) so that said intermediate portion can be inserted into said counterbore of said screw with a sliding fit and (ii) so that when said intermediate portion is inserted in said counterbore said intermediate portion drivingly engages said counterbore so that rotational drive can be transmitted from said driver to said screw, and
  (c) a cylindrical front portion having a back end and a front end, said back end of said front portion being fixedly attached to said first end of said intermediate portion, said front portion comprising compression means for permitting said front portion to be compressed radially into a compressed state, the design and diameter of said cylindrical front portion being chosen (i) so that insertion of said front portion into said bore of said screw causes said front portion to be compressed into said compressed state, and (ii)

so that when said front portion is inserted in said bore said front portion engages said bore with a spring interference fit, whereby said front portion cannot be removed from said bore except when a selected axial force is applied to said front portion.

23. A driver for use in conjunction with a screw of the sort comprising (a) first and second ends, (b) an axial bore coupled with said first end, said axial bore having a circular cross section of selected diameter, and (c) a counterbore coupled with said first end and coaxial with said axial bore, said counterbore having a selected length and a polygonal cross section of selected configuration and dimension, said driver comprising:
  (a) an elongate shaft having a front end,
  (b) an elongate intermediate portion having first and second ends, said second end of said intermediate portion being fixedly attached to said front end of said shaft, said intermediate portion having a polygonal cross section configured and dimensioned (i) so that said intermediate portion of said driver can be inserted into said counterbore of said screw with a sliding fit and (ii) so that when said intermediate portion of said driver is inserted in said counterbore of said screw said intermediate portion of said driver will drivingly engage said counterbore of said screw so that rotational driver can be transmitted from said driver to said screw, and
  (c) a cylindrical front portion having a back end and a front end, said back end of said front portion being fixedly attached to said first end of said intermediate portion, said front portion comprising compression means for permitting said front portion to be compressed radially into a compressed state, the design and diameter of said cylindrical front portion being chosen (i) so that insertion of said front portion of said driver into said bore of said screw will cause said front portion of said driver to be compressed into said compressed state, and (ii) so that when said front portion of said driver is inserted in said bore of said screw said front portion of said driver will engage said bore of said screw with a spring interference fit, whereby said front portion of said driver cannot be removed from said bore of said screw except when a selected axial force is applied to said front portion of said driver.

24. A method of installing a screw into a bone, said method comprising the steps of:
  (1) providing a screw and a driver wherein:
  said screw comprises:
    (a) first and second ends,
    (b) an axial bore coupled with said first end, said axial bore having a circular cross section of selected diameter, and
    (c) a counterbore coupled with said first end and coaxial with said axial bore, said counterbore having a selected length and a polygonal cross section of selected configuration and dimension, and
  said driver comprises:
    (a) an elongate shaft having a front end,
    (b) an elongate intermediate portion having first and second ends, said second end of said intermediate portion being fixedly attached to said front end of said shaft, said intermediate portion having a polygonal cross section configured and dimensioned (i) so that said intermediate portion of said driver can be inserted into said counterbore of said screw with a sliding fit, and (ii) so that when said intermediate portion of said driver is inserted in said counterbore of said screw said intermediate portion drivingly engages said counterbore of said screw so that rotational drive can be transmitted from said driver to said screw, and
    (c) a cylindrical front portion having a back end and a front end, said back end of said front portion being fixedly attached to said first end of said intermediate portion, said front portion comprising compression means for permitting said front portion to be compressed radially into a compressed state, the design and diameter of said cylindrical front portion being chosen (i) so that insertion of said front portion into said bore of said screw ill cause said front portion of said driver to be compressed into said compressed state, and (ii) so that when said front portion of said driver is inserted in said bore of said screw said front portion will engage said bore with a spring interference fit, whereby said front portion of said driver cannot be removed from said bore of said screw except when a selected axial force is applied to said front portion of said driver;
  (2) attaching said screw to said driver by inserting said front portion of said driver into said bore of said screw and said intermediate portion of said driver into said counterbore of said screw;
  (3) installing said screw into said bone by pressing said second end of said screw against said bone and rotating said driver so that said screw is driven into said bone; and
  (4) detaching said driver from said screw by moving said driver away from said bone.

25. A method of installing a screw into a bone, said method comprising the steps of:
  (1) providing a guide wire, a screw and a driver wherein:
  said guide wire comprises first and second ends and has a circular cross section of a selected diameter,
  said screw comprises:
    (a) first and second ends,
    (b) an axial bore extending through the entire length of said screw, said axial bore having a circular cross section of a selected diameter, wherein said selected diameter of said axial bore is greater than said selected diameter of said guide wire, and
    (c) a counterbore coupled with said first end and coaxial with said axial bore, said counterbore having an inner axial portion with a circular cross section of selected diameter, and an outer axial portion coupled with said first end and having a polygonal cross section of selected configuration and dimension, and
  said driver comprises:
    (a) an elongate shaft having a front end,
    (b) an elongate intermediate portion having first and second ends, said second end of said intermediate portion being fixedly attached to said front end of said shaft, said intermediate portion having a polygonal cross section configured and dimensioned (i) so that said intermediate portion of said driver can be inserted into said outer axial portion of said counterbore of said screw with a sliding fit, and (ii) so that when said intermediate portion of said driver is inserted in said outer axial portion of said counterbore of said screw said intermediate portion drivingly engages said outer axial portion of said counterbore of said screw so that rotational drive can be transmitted from said driver to said screw, and (c) a cylindrical front portion having a back end and a front end, said back end of said front portion being fixedly attached to said first end of said intermediate portion, said front portion comprising compression means for permitting said front portion to be compressed radially into a compressed state, the design and diameter of said cylindrical front portion being chosen (i) so that insertion of said front portion into said inner axial portion of said counterbore of said screw will cause said front portion of said driver to be compressed into said compressed state, and (ii) so that when said front portion of said driver is inserted in said inner axial portion of said counterbore of said screw said front portion will engage said inner axial portion of said counterbore with a spring interference fit, whereby said front portion of said driver cannot be removed from said inner axial portion of said counterbore of said screw except when a selected axial force is applied to said front portion of said driver, and (d) an axial bore extending through the entire length of said driver, said axial bore having a circular cross section of a selected diameter, wherein said selected diameter of said axial bore is greater than said selected diameter of said guide wire, and (2) installing said guide wire in said bone by inserting said second end of said guide wire into said bone so that said first end of said guide wire is disposed remote from said bone, and attaching said screw to said driver by inserting said front portion of said driver into said inner axial portion of said counterbore of said screw and said intermediate portion of said driver into said outer axial portion of said counterbore of said screw;

(3) loading said screw and said driver onto said guide wire by passing said first end of said guide wire through said axial bore of said screw and said axial bore of said driver, (4) installing said screw into said bone by moving said screw and said driver along said guide wire toward said bone until said second end of said screw is pressed against said bone and then rotating said driver so that said screw is driven into said bone; and (5) detaching said driver from said screw by moving said driver along said guide wire from said bone.

26. An elongate screw for use in conjunction with a driver of the sort comprising (a) an elongate shaft having a front end, (b) an elongate intermediate portion having first and second ends, said second end of said intermediate portion being fixedly attached to said front end of said shaft and said intermediate portion having a polygonal cross section, and (c) a front portion having a back end and a front end, said back end of said front portion being fixedly attached to said first end of said intermediate portion, and said front portion comprising compression means for permitting said front portion to be compressed radially into a compressed state, said elongate screw comprising:

(a) a shaft having first and second ends and a threaded exterior surface;

(b) an axial bore adapted to receive a guide wire therethrough, said axial bore extending through said shaft and coupled with said first and second ends respectively, said axial bore having a substantially constant transverse cross section;

(c) a blind axial bore coaxial with said axial bore, said blind axial bore having an outer portion coupled with said first end of said shaft and an inner portion terminating in a shoulder, said inner portion of said blind axial bore having a cross section larger than the cross section of said axial bore and selected (i) so that insertion of said front portion of said driver into said inner portion of said blind axial bore in said screw will cause said front portion of said driver to be compressed into said compressed state, and (ii) so that when said front portion of said driver is inserted in said inner portion of said blind axial bore in said screw, said front portion of said driver will engage said inner portion of said blind axial bore with a spring interference fit, whereby said front portion of said driver cannot be removed from said inner portion of said blind axial bore of said screw except when a selected axial force is applied to said front portion of said driver; and (d) a counterbore disposed about said outer portion of said blind axial bore, coupled with said first end of said shaft and coaxial with said axial bore, said counterbore having a constant polygonal cross section chosen (i) so that when said front portion of said driver is fully inserted into said inner portion of said blind axial bore, said intermediate portion of said driver engages said counterbore of said screw with a sliding fit, and (ii) so that when said intermediate portion of said driver engages said counterbore of said screw, said intermediate portion of said driver is in driving relation to said counterbore so that rotational drive can be transmitted from said driver to said screw.

* * * * *

UNITED STATES PATENT AND TRADEMARK OFFICE
CERTIFICATE OF CORRECTION

PATENT NO. : 5,139,499
DATED : August 18, 1992
INVENTOR(S) : Alan A. Small and Bernard J. Bourque It is certified that error appears in the above-indentified patent and that said Letters Patent is hereby corrected as shown below:

Claim 21, line 01, "claim 10" should read --claim 20--.

Signed and Sealed this

Twenty-fifth Day of August, 1998

*Attest:*

*Attesting Officer*

BRUCE LEHMAN

*Commissioner of Patents and Trademarks*